(12) United States Patent
Titchener

(10) Patent No.: US 8,652,065 B2
(45) Date of Patent: Feb. 18, 2014

(54) BREATHING TRANSITION DETECTION

(75) Inventor: Mark Renfrew Titchener, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 330 days.

(21) Appl. No.: 13/030,868

(22) Filed: Feb. 18, 2011

(65) Prior Publication Data

US 2011/0230779 A1    Sep. 22, 2011

Related U.S. Application Data

(63) Continuation of application No. PCT/NZ2009/000172, filed on Aug. 19, 2009.

(60) Provisional application No. 61/089,961, filed on Aug. 19, 2008.

(51) Int. Cl.
    *A61B 5/08*    (2006.01)
(52) U.S. Cl.
    USPC ........................................................ 600/538
(58) Field of Classification Search
    USPC .................... 600/538; 128/204.18, 204.23
    See application file for complete search history.

(56) References Cited

U.S. PATENT DOCUMENTS

| | | | |
|---|---|---|---|
| 5,355,893 A | 10/1994 | Mick et al. | |
| 5,794,615 A | 8/1998 | Estes | |
| 5,941,710 A * | 8/1999 | Lampotang et al. | 434/272 |
| 6,237,593 B1 | 5/2001 | Brydon | |
| 6,318,365 B1 | 11/2001 | Vogele et al. | |
| 6,910,480 B1 | 6/2005 | Berthon-Jones | |
| 7,089,936 B2 * | 8/2006 | Madaus et al. | 128/204.23 |
| 2002/0185131 A1 | 12/2002 | Madaus et al. | |
| 2005/0211248 A1 * | 9/2005 | Lauk et al. | 128/204.23 |
| 2006/0276718 A1 * | 12/2006 | Madaus et al. | 600/538 |

FOREIGN PATENT DOCUMENTS

| | | |
|---|---|---|
| EP | 076808 A1 | 4/1996 |
| WO | WO 02/094358 | 11/2002 |

OTHER PUBLICATIONS

Han, J. et al, "Detection of Apneic Events From Single Channel Nasal Airflow Using 2nd Derivative Method", Computer Methods and Programs in Biomedicine, 2008, 91, 199-207.
Korten, J.B. et al., "Respiratory Waveform Pattern Recognition Using Digital Techniques", Comput. Biol. Med., 1989, 19(4), 207-217.
Skeffington W.M. et al, "Evaluation of Respiratory Triggering Algorithms", Proc. Intl. Soc. Mag. Reson. Med., 2004, 11, 2147.
International Search Report and written opinion received in PCT/NZ2009/000172 mailed on Dec. 7, 2009 in 12 pages.

* cited by examiner

*Primary Examiner* — Navin Natnithithadha
*Assistant Examiner* — Etsub Berhanu
(74) *Attorney, Agent, or Firm* — Knobbe Martens Olson & Bear LLP

(57) ABSTRACT

Detecting transitions in a breathing cycle which includes using a second derivative 54 of a flow waveform 51 to find breathing transitions 51*c* in the waveform 51.

6 Claims, 10 Drawing Sheets

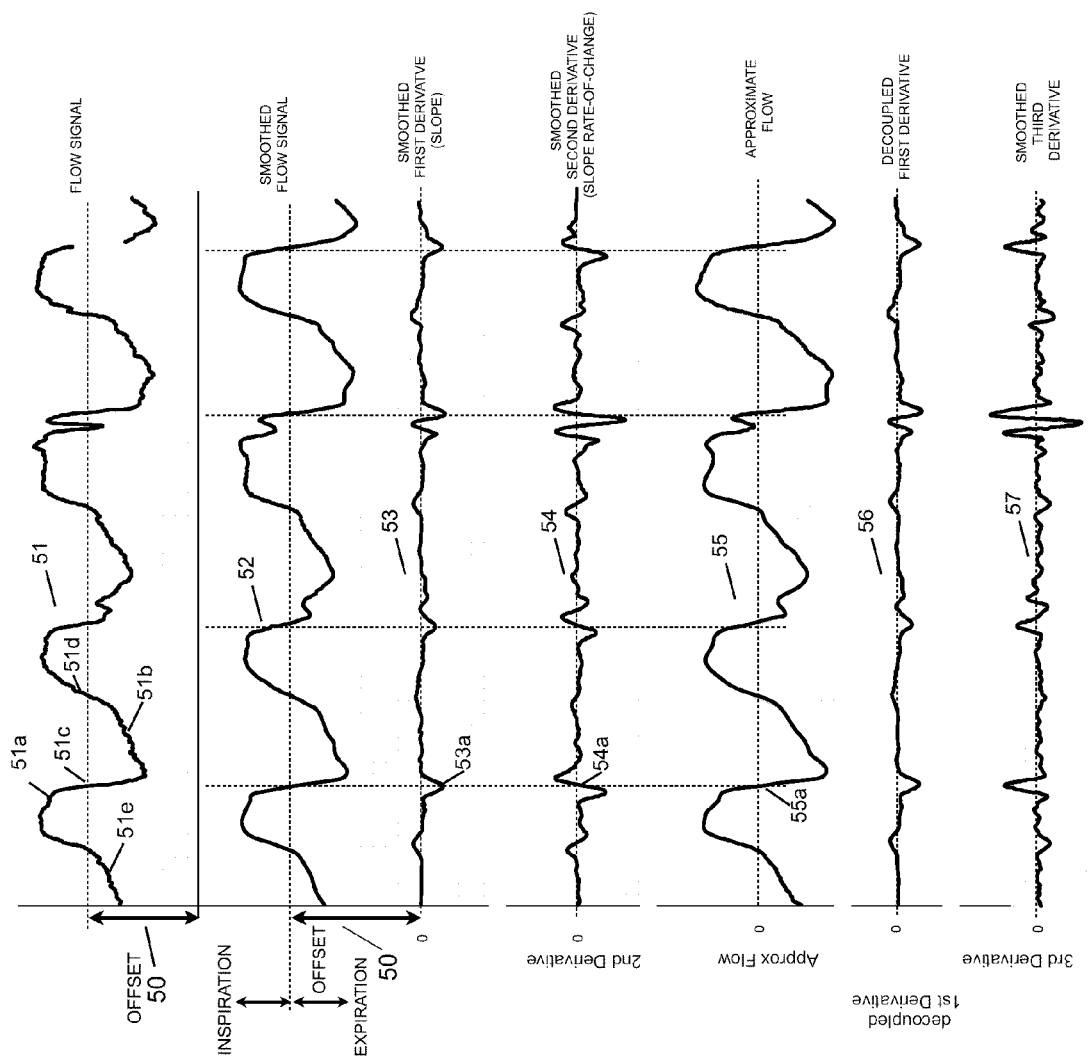

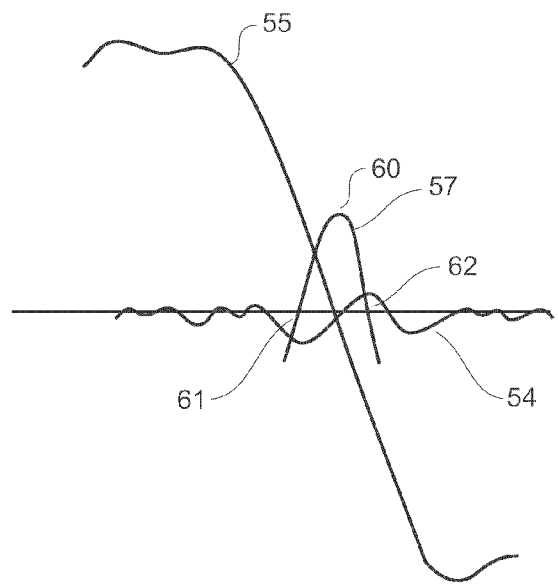
FIGURE 6
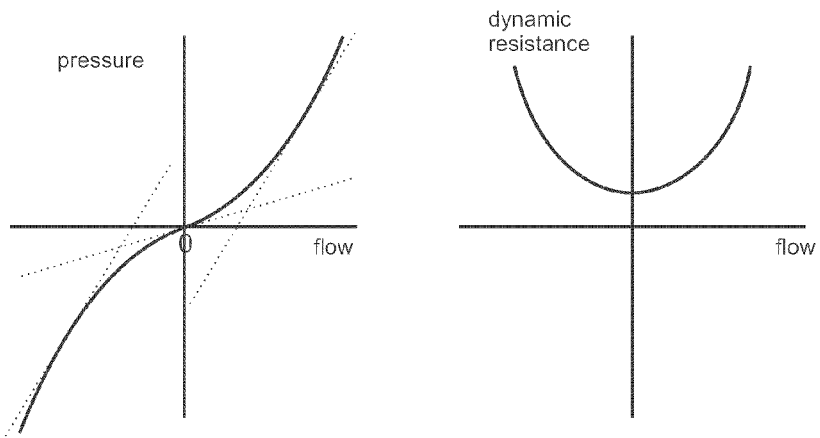
FIGURE 7        FIGURE 8

BREATHING TRANSITION DETECTION

CROSS-REFERENCE TO RELATED APPLICATIONS

This application is a continuation under 35 U.S.C. §120 of PCT International Application No. PCT/NZ2009/000172, filed Aug. 19, 2009, which claims priority to U.S. Provisional Application No. 61/089,961, filed Aug. 19, 2008, each of which are incorporated by reference in their entirety.

FIELD OF THE DISCLOSURE

The present disclosure relates to the field of positive pressure assistance devices and more specifically to determining a transition between inspiration and expiration.

BACKGROUND

Obstructions in some patient's airways during sleep can cause limited airflow, leading to apnoea, hypopnoea or snoring. The obstruction is often a collapsed pharynx. The obstruction may be a partial airway obstruction, leading to altered characteristics of the airflow. A hypopnea is a reduction of the flow that is greater than fifty percent, but not complete. An apnea, however, is complete cessation of airflow. Each of these conditions frequently leads to sleep deprivation and other associated health problems.

It is well known to treat patient suffering from sleep deprivation with positive airway pressure therapy ("PAP"). This therapy can be Continuous Positive Airway Pressure ("CPAP"), Variable Positive Airway Pressure ("VPAP"), Bi-level Positive Airway Pressure ("BiPAP"), Auto titrating Positive Airway Pressure ("APAP") or any numerous other forms of respiratory therapy. The application of positive pressure to the patient's pharynx helps minimize or prevent this collapse. Positive airway pressure therapy is currently supplied by means of an apparatus containing a pressure source, typically a blower, through a tube to an interface or mask, which the patient wears while sleeping.

Control the applied pressure is an important consideration in PAP. Too little pressure tends not to solve the problem. Too much pressure tends to cause discomfort to the patient, such as drying out of the mouth and pharynx, as well as difficulty in exhaling against the applied pressure.

One solution to this problem is to use a bi-level devices which tracks pressure in accordance with a patient's inspiration and expiration. However, an accurate indication of the change from inspiration to expiration is necessary.

It is also desirable to be able to adjust the applied pressure without requiring the patient to attend a sleep centre, so the apparatus will allow in-home adjustments, preferably automatically. One method generally thought to be effective is to monitor the patient to try to anticipate the onset of an obstructed airway, and to adjust the pressure in response. When an elevated upper airway resistance or flow obstruction is anticipated or underway, the apparatus increases the applied pressure. When the patient returns to normal sleep, the applied pressure is reduced.

For bi-level control of an apparatus, that is, matching of pressure with a patient's inspiratory and expiratory breathing flows, the air pressure is supplied at a higher pressure during inspiration and at a lower pressure during expiration. This makes it easier for the patient to breath against the lower pressure during exhalation.

A patient's respiratory flow when measured in the absence of an applied pressure or flow clearly reveals respiratory phases and the transition between expiration and inspiration. In FIG. 1 inspiration is that part of the waveform above the axis and expiration corresponds to that area below the axis. Where the waveform crosses zero indicates the transition points between the phases. That is, the transition point is where the patient changes from inspiration to expiration, or vice versa.

When a patient is breathing through a mask and is supplied with positive airway pressure the air flow waveform that may be recorded is displaced away from the axis by the application of an external flow, as shown FIG. 2, for example. It is difficult to extract inspiratory and expiratory phases and transitions accurately where there is a displacement and without reference to the flow signal itself. Usually the flow signal itself does not provide an obvious indicator of the transition between expiration and inspiration and vice versa. The waveform, for example, does not cross zero at the inspiration/expiration nor at expiration/inspiration transitions.

SUMMARY

The present disclosure relates to apparatus, methods and/or software for determining breathing transitions, such as the inspiration to expiration transition. This can form part of or be used in conjunction with a breathing apparatus for treating sleep apnea. More specifically, it can form part of or be used in conjunction with an apparatus that provides an interface for the supply of respiratory gases, but most particularly positive pressure gases.

In one aspect, the present disclosure includes a method of determining the transition between inspiration and expiration of a patient's respiratory cycle including measuring a patient's respiratory flow to obtain a flow waveform indicative of the respiratory flow, obtaining a second derivative of the flow waveform or part thereof, and determining an inspiration/expiration transition of the patient's respiratory flow by identifying the steepest descent of the flow waveform using the second derivative of the flow waveform.

In an embodiment, determining an inspiration/expiration transition of the patient's respiratory flow using the second derivative includes using a negative to positive zero crossing in the second derivative. In an embodiment, the flow waveform has an offset removed and further including determining a zero crossing of the flow waveform, where using a negative to positive zero crossing in the second derivative includes using a negative to positive zero crossing in the second derivative that corresponds to the zero crossing in the flow waveform.

In an embodiment, the method includes obtaining a third derivative of the flow waveform or part thereof, where using a negative to positive zero crossing in the second derivative includes using a negative to positive zero crossing in the second derivative that corresponds to the zero crossing in the flow waveform and a positive portion of the third derivative that coincides with the flow waveform and second derivative zero crossings.

In an embodiment, removing an offset from the flow waveform includes obtaining a first derivative of the flow waveform, removing a DC offset from the first derivative, and integrating the first derivative with the DC offset removed.

In an embodiment, the method further includes determining an expiration to inspiration transition by determining the level of the determined inspiration to expiration transition in the flow waveform, and finding a previous or subsequent portion of the flow waveform that increases from below to above the level.

In an embodiment, the method further includes determining an inspiration or expiration respiratory phase from adjacent expiration/inspiration and inspiration/expiration transitions, and controlling delivery of respiratory gases to a patient depending on the determined respiratory phase In an embodiment, determining multiple inspiration/expiration transition of the patient's respiratory flow includes determining multiple transitions.

In an embodiment, the method further includes using the determined expiration/inspiration and/or inspiration/expiration respiratory phases to determine the patient's state.

In an embodiment, the method further includes using the determined expiration/inspiration respiratory phases to control breathing apparatus operation.

In another aspect the present disclosure describes a method of determining the transition between inspiration and expiration of a patient's respiratory cycle including measuring a patient's respiratory flow to obtain a flow waveform indicative of the respiratory flow from a breathing apparatus, obtaining a second derivative of the flow waveform or part thereof, and determining an inspiration/expiration transition of the patient's respiratory flow by identifying the steepest descent of the flow waveform using the second derivative of the flow waveform.

In another aspect the present disclosure describes a method of determining the transition between inspiration and expiration of a patient's respiratory cycle including measuring a patient's respiratory flow to obtain an electrical signal representing the respiratory flow, obtaining a second derivative of the electrical signal or part thereof, and determining an inspiration/expiration transition of the patient's respiratory flow by identifying the steepest descent of the flow waveform using the second derivative of the electrical signal.

In another aspect the present disclosure describes a system for determining the transition between inspiration and expiration of a patient's respiratory cycle including a flow sensor for measuring a patient's respiratory flow to obtain a flow waveform indicative of the respiratory flow, an electronic device to determine a second derivative of the flow waveform or part thereof, and to determine an inspiration/expiration transition of the patient's respiratory flow by identifying the steepest descent of the flow waveform using the second derivative of the flow waveform.

In an embodiment, to determine an inspiration/expiration transition of the patient's respiratory flow using the second derivative, the electronic device uses a negative to positive zero crossing in the second derivative.

In an embodiment, the flow waveform has an offset and the electronic device is adapted to detect a zero crossing of the flow waveform without an offset, wherein to use a negative to positive zero crossing in the second derivative the electronic device uses a negative to positive zero crossing in the second derivative that corresponds to the zero crossing in the flow waveform.

In an embodiment, the electronic device obtains a third derivative of the flow waveform or part thereof, wherein to use a negative to positive zero crossing in the second derivative the electronic device uses a negative to positive zero crossing in the second derivative that corresponds to the zero crossing in the flow waveform and a positive portion of the third derivative that coincides with the flow waveform and second derivative zero crossings.

In another aspect the present disclosure describes a method of determining the transition between inspiration and expiration of a patient's respiratory cycle including measuring a patient's respiratory flow to obtain a flow waveform indicative of the respiratory flow, sampling the flow waveform (or waveform processed therefrom) using negative to positive zero crossings of a second derivative of the flow waveform, selecting one of the samples using a third derivative of the flow waveform as a trigger, the selected sample identifying a breathing transition.

In an embodiment, a positive to negative zero crossing of the third derivative is used as the trigger.

In another aspect the present disclosure includes a system for determining the transition between inspiration and expiration of a patient's respiratory cycle including a flow sensor for measuring a patient's respiratory flow to obtain a flow waveform indicative of the respiratory flow, an electronic device to sample the flow waveform (or waveform processed there from) using negative to positive zero crossings of a second derivative of the flow waveform, and to select one of the samples using a third derivative of the flow waveform as a trigger, the selected sample identifying a breathing transition.

In an embodiment, a positive to negative zero crossing of the third derivative is used as the trigger.

In one aspect the present disclosure describes in a method of determining the transition between inspiration and expiration of a patient's respiratory cycle including measuring a patient's respiratory flow to obtain a flow waveform indicative of the respiratory flow, determining the point or region of steepest decent of the flow waveform, and determining the occurrence of an inspiration/expiration transition of the patient's respiratory flow from the point or region of steepest descent of the flow waveform.

In an embodiment, determining the point or region or steepest decent of the flow waveform includes obtaining a second derivate of the flow waveform, and determining a negative to positive zero crossing in the second derivative.

In an embodiment, determining the point of region or steepest decent of the flow waveform includes obtaining a first derivate of the flow waveform, and determining a negative peak in the first derivative.

In another aspect the present disclosure describes a method of determining the transition between inspiration and expiration of a patient's respiratory cycle for use in controlling delivery of respiratory gases to a patient including measuring the patient's respiratory flow and, from the measuring, obtaining a flow waveform indicative of the patient's respiratory flow, processing the flow waveform to obtain first and/or second derivatives of the flow waveform, and determining one or more inspiration/expiration transitions by identifying the steepest descent in the flow waveform, from the flow waveform, first derivative of the flow waveform and/or second derivative of the flow waveform.

In an embodiment, the method further includes using the determined expiration/inspiration and/or inspiration/expiration respiratory phases to determine the patient's state.

In an embodiment, the method further includes determining the occurrence of one or more inspiration phases and one or more expiration phases of the patient's respiratory flow from the one or more inspiration/expiration transitions.

In an embodiment, the method further includes controlling pressure, humidity and/or flow of respiratory gases to/from the patient in response to the occurrence of inspiration phases and/or expiration phases of the patient's respiratory flow.

In an embodiment, an inspiration to expiration transition is determined in a portion of the patient's respiratory flow if the flow waveform corresponding to that portion has a second derivative that crosses zero from negative to positive.

In an embodiment, an inspiration to expiration transition is determined in a portion of the patient's respiratory flow if the flow waveform corresponding to that portion has a negative peak in the first derivative.

In an embodiment, the method further includes determining an expiration to inspiration transition by determining the level of the determined inspiration to expiration transition in the flow waveform, and finding a previous or subsequent portion of the flow waveform that increases from below to above the level.

In an embodiment, an expiration phase is determined as occurring between an inspiration to expiration transition followed by an expiration to inspiration transition.

In an embodiment, an inspiration phase is determined as occurring between an expiration to inspiration transition followed by an inspiration to expiration transition.

In another aspect the present disclosure includes a breathing assistance apparatus including a controller for operating the apparatus to control delivery of respiratory gases to a patient, controller being adapted to obtain measurements on the patient's respiratory flow, from the measurements, obtain a flow waveform indicative of the patient's respiratory flow, process the flow waveform to obtain first and/or second derivatives of the flow waveform, and determine one or more inspiration/expiration transitions by identifying the steepest descent in the flow waveform, from the flow waveform, first derivative of the flow waveform and/or second derivative of the flow waveform.

In an embodiment, the controller is further adapted to determine the occurrence of one or more inspiration phases and one or more expiration phases of the patient's respiratory flow from the one or more inspiration/expiration transitions.

In an embodiment, the controller is further adapted to control pressure, humidity and/or flow of respiratory gases to/from the patient in response to the occurrence of inspiration phases and/or expiration phases of the patient's respiratory flow.

In an embodiment, the controller is further adapted use the determined expiration/inspiration and/or inspiration/expiration respiratory phases to determine the patient's state.

In an embodiment, an inspiration to expiration transition is determined in a portion of the patient's respiratory flow if the flow waveform corresponding to that portion has a negative first derivative and a second derivative that crosses zero from negative to positive.

In an embodiment, an expiration to inspiration transition is determined in a portion of the patient's respiratory flow if the flow waveform corresponding to that portion has a positive first derivative and a second derivative that crosses zero from positive to negative.

In an embodiment, an expiration phase is determined as occurring between an inspiration to expiration transition followed by an expiration to inspiration transition.

In an embodiment, an inspiration phase is determined as occurring between an expiration to inspiration transition followed by an inspiration to expiration transition.

In one aspect the present disclosure describes method of determining the transition between inspiration and expiration of a patient's respiratory cycle including measuring an electrical signal indicating patient's respiratory flow, the electrical signal specifying a flow waveform indicative of the respiratory flow, determining the point or region of steepest decent of the electrical signal, and determining the occurrence of an inspiration/expiration transition of the patient's respiratory flow from the point or region of steepest decent of the flow waveform.

In a another aspect the present disclosure describes a breathing assistance apparatus including a controller for operating the apparatus to control delivery of respiratory gases to a patient, controller being adapted to obtain measurements on the patient's respiratory flow, the measurements forming an electrical signal specifying a flow waveform indicative of the patient's respiratory flow, process the signal to obtain first and/or second derivatives of the electrical signal, and determine one or more inspiration/expiration transitions by identifying the steepest descent in the flow waveform from the electrical signal, first derivative of the electrical signal and/or second derivative of the electrical signal.

In another aspect the present disclosure describes a method of determining the breathing state of a person and is characterized in that the first and the second derivative of an electrical signal representing the persons breathing are determined and that the breathing situation is determined based on this first and second derivative.

In an embodiment, the electrical signal is first smoothed by a low pass filter, to remove noise. In an embodiment, smoothing is achieved by a least squares fit of sample points to a low order polynomial within a sliding window wherein the polynomial coefficients also provide samples of the smoothed first and smoothed second derivatives.

In an embodiment, the first derivative of the electrical signal is DC decoupled and again integrated to generate a smoothed approximate flow signal without a DC offset and in which the positive and negative zero crossing transitions may be used to determine a first and second point in time corresponding closely to the changes of the breathing from expiration to inspiration, and vice versa.

In an embodiment, the first derivative is compared with a first threshold value, in order to determine a first interval which encloses the end of an inspiration phase and with a second threshold value in order to determine a second interval which encloses the end of an expiration phase. If no zero crossings occur at all, this means that there is an apnea situation.

According to a further aspect of the disclosure, zero crossings are determined for the second derivative of the electrical signal within the first interval and within the second interval, for precisely determining the end of an inspiration phase or the end of an expiration phase respectively.

Airflow will have a strong amplitude modulation when a person is snoring. Therefore, according to a further aspect of the disclosure, the first derivative of the electrical signal is rectified during the inspiration phase and subsequently compared with a third threshold, for determining a snoring situation.

It has been noticed that the flow of air during the expiration phase consists of two sub phases having different slopes. In an embodiment, the smoothed second derivative of the electrical signal is used to locate the point in time when the slope changes and the degree of fluctuation, or conversely the stability from breath to breath in the flow level at the point in time where the change in slope occurs is used for determining if a person is awake or asleep.

In another aspect the present disclosure describes a method of determining the transition between inspiration and expiration of a patient's respiratory cycle including measuring a patient's respiratory flow to obtain a flow waveform indicative of the respiratory flow, determining the zero-crossing of the flow waveform without offset, and determining the occurrence of an inspiration/expiration transition of the patient's respiratory flow from the point or region of zero-crossing.

In this specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

This disclosure may also be said broadly include in the parts, elements and features referred to or indicated in the specification of the application, individually or collectively, and any or all combinations of any two or more of said parts, elements or features, and where specific integers are mentioned herein which have known equivalents in the art to which this disclosure relates, such known equivalents are incorporated herein as if individually set forth.

The disclosure consists in the foregoing and also envisages constructions of which the following gives examples.

BRIEF DESCRIPTION OF THE DRAWINGS

Embodiments of the present disclosure will now be described with reference to the accompanying drawings.

FIG. 4b illustrates a block diagram of a system for implementing the method of FIG. 4a.

FIGS. 5a to 5g illustrate the flow waveform, smoothed flow waveform, its first and second derivative waveforms, approximate flow waveform, the decoupled first derivative, and the relationships between these and the transition from inspiration to expiration.

FIG. 6 illustrates the approximate flow waveform, and second and third derivatives in the area of the transition.

FIG. 7 illustrates the pressure versus flow function for the airways tract and lung. The slope of the transfer function corresponds to the dynamic resistance to flow during the respiratory phases.

FIG. 8 graphs the dynamic resistance corresponding to the pressure versus flow curve in FIG. 7, indicating that a minimum occurs at the transition from inspiration to expiration. At the onset of the transition from inspiration to expiration during which the passive elastic collapse of the lung provides a near constant driving force, the occurrence of the minimum in the dynamic resistance effectively gives rise to the transition from inspiration to expiration coinciding with the steepest descent in the flow signal.

DETAILED DESCRIPTION

An embodiment of the disclosure relates generally to an apparatus, software and/or method for detecting transitions in patient respiration. One embodiment detects the steepest decent in a patient's breathing flow waveform to determine an occurrence of an inspiration to expiration transition. The method of the present disclosure as described in the embodiments of this disclosure can be used in respiratory care generally. It is described below with reference to use in a humidified Positive Airway Pressure (PAP) system. It will be appreciated, however, that the present disclosure can be used in any application where it is beneficial to detect breathing transitions in order to control the operation of respiratory apparatus for better operation.

Figure 1:
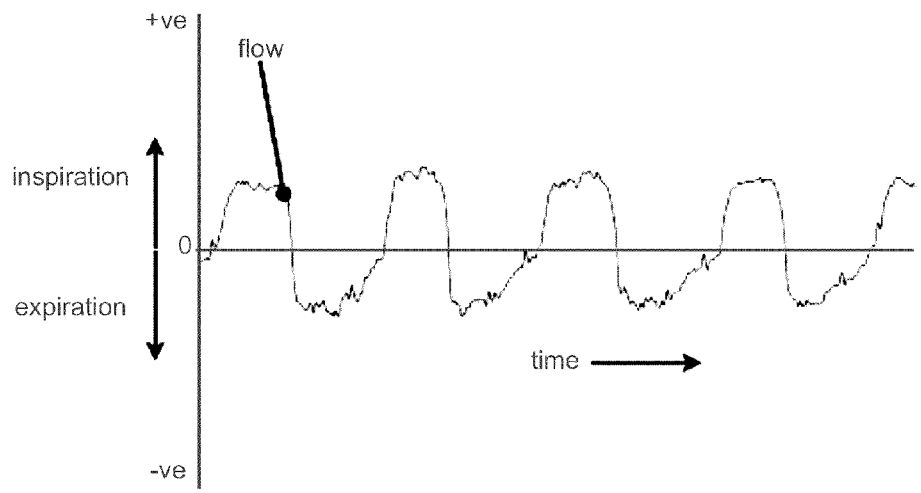
FIG. 1 illustrates a typical flow waveform of a patient's breathing, showing the positive flow inspiration and negative flow expiration breathing phases.
Figure 2:
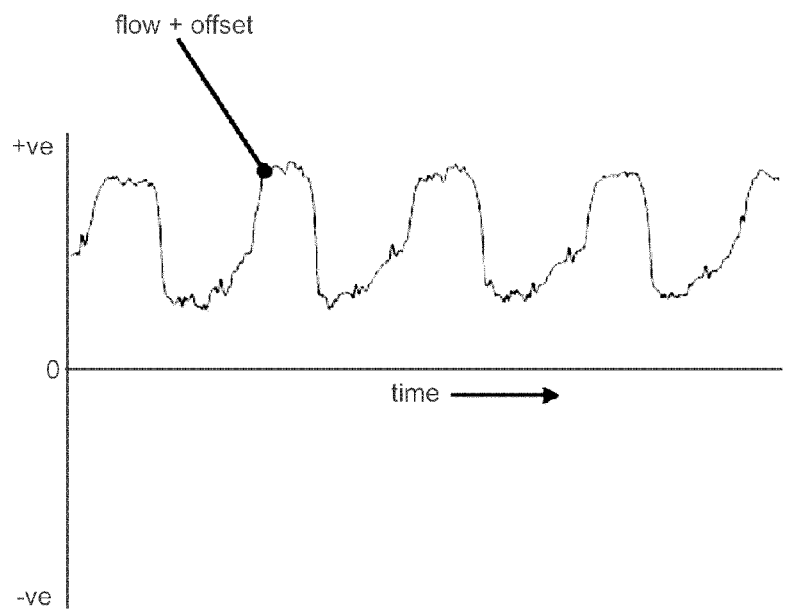
FIG. 2 illustrates the flow waveform recorded with a quiescent flow offset, more typical of a CPAP application.
Figure 3:
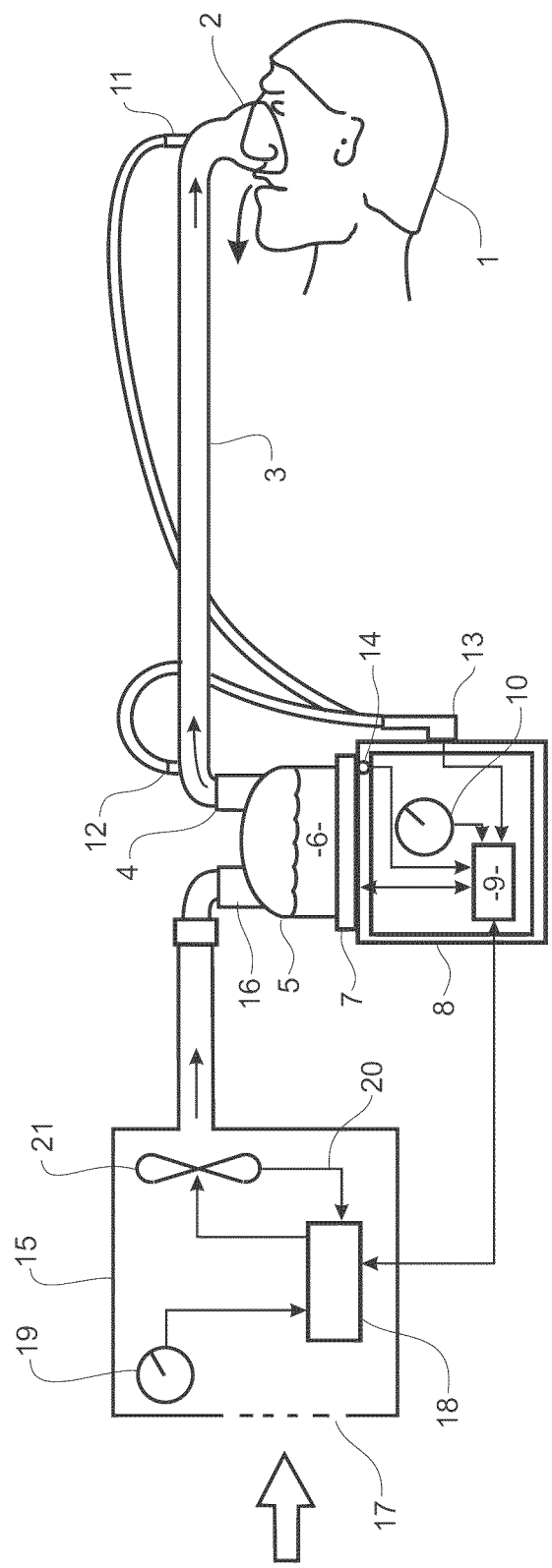
FIG. 3 is a block diagram of a humidified positive airway pressure (system) as might be used in conjunction with a method of the present disclosure.

A humidified Positive Airway Pressure (PAP) system is shown FIG. 3 in which a patient 1 is receiving humidified and pressurized gases through a patient interface (nasal mask) 2 connected to a humidified gases transportation pathway or inspiratory conduit 3. The inspiratory conduit 3 is connected to an outlet 4 of a humidification chamber 5 that contains a volume of water 6. The inspiratory conduit 3 can contain a heater or heater wires (not shown) that heat the walls of the conduit to reduce condensation of humidified gases within the conduit.

The humidification chamber 6 is preferably formed from a plastics material and preferably has a highly heat conductive base (for example an aluminum base) that is in direct contact with a heater plate 7 of humidifier 8. The humidifier 8 is provided with control system or an electronic controller 9 that can include a microprocessor based controller executing computer software commands stored in associated memory.

The controller 9 receives input from sources such as a user input or a dial 10 through which a user of the device can, for example, set a predetermined required value (preset value) of humidity or temperature of the gases supplied to patient 1. The controller 9 can also receive input from other sources, for example temperature and/or flow velocity sensors 11, 12, through a connector 13 and a heater plate temperature sensor 14. In response to the user set humidity or temperature value input via the dial 10 and the other inputs, the controller 9 determines when (or to what level) to energize the heater plate 7 to heat the water 6 within the humidification chamber 5. As the volume of the water 6 within the humidification chamber 5 is heated, water vapor begins to fill the volume of the chamber above the water's surface and is passed out of the humidification chamber 5 outlet 4 with the flow of gases (for example air) provided from a gases supply means or blower 15 that enters the chamber 5 through an inlet 16. Exhaled gases from the patient's mouth are passed directly to the ambient surroundings in FIG. 3.

The blower 15 is provided with a variable pressure regulating system or variable speed fan 21 that draws air or other gases through a blower inlet 17. The speed of the variable speed fan 21 is controlled by an electronic controller 18 (or alternatively the function of the controller 18 can carried out by the controller 9) in response to inputs from the controller 9 and a user set predetermined required value (preset value) of pressure or the fan speed via dial 19.

The blower 15 and humidifier 8 including chamber 6 may be an integrated unit.

In an embodiment, the blower unit includes controllers 9 or 18 that control when and at what level pressure is applied to the mask. For example, the blower unit and controllers are capable of controlling the gases pressure such that it is a low pressure when the patient is exhaling and a higher pressure when the patient is inhaling. In order to implement this type of control the unit needs to know when the transition between inspiration and expiration occurs for the patient's breathing.

The Applicant experimented with a purpose built spirometer to measure displacement in an integrated flow. Various derivatives of a flow were determined. The Applicant measured his own flow when a pressure had been applied to his breathing tracts. He found that the point of steepest descent in the flow waveform reliably coincides with the transition between inspiration (positive flow) and expiration (negative flow) under wide ranging conditions. This is because the flow resistance to the lung is strongly non-linear. The pressure versus flow characteristic for the respiratory airways is depicted in FIG. 7. The slope of the transfer function in FIG. 7 represents the resistance to flow as a function of flow. The present disclosure uses to its advantage the existence of this non-linear transition which ultimately arises from the staged transition from laminar to turbulent flow that occurs naturally in a person's airways during respiration. The transition to turbulent flow gives rise to increases in resistance that is a function of not only the level of flow, but also the airways diameter and branching topologies. This results in the non-linear dynamic resistance (pressure versus flow) characteristic of FIG. 7. The resistance falls to a minimum at the point when the flow itself tends to zero, i.e., at the transition from inspiration to expiration and from expiration to inspiration. In particular, during the transition from inspiration to expiration the lung dynamics behave largely as a passive driven elastically sprung cavity. This, together with the non-linear dynamic resistance, results in the steepest descent in the flow correlating to the transition from inspiration to expiration, when the sprung lung chamber deflates passively.

The Applicant then went onto use this observation to extract the inspiratory and expiratory phases of patient breathing. The method and/or apparatus of the present disclosure enables the extraction of the respiratory phases (inspiration/expiration) when a slow changing or fixed flow offset is applied to a patient's respiratory passages. The flow offset may be brought about by the external application of a flow, such as a positive airways pressure, continuous, bi-level, automatic or otherwise.

An expiratory phase is where the patient breathes out 51b. This occurs at a negative portion 51b in a flow waveform 51, for example as shown in FIG. 5a. The expiratory phase occurs between the inspiration to expiration transition (see e.g. 51c) and the expiration to inspiration transition (see e.g. 51d). An inspiratory phase is when the patient is breathing in 51a. This occurs at a positive portion 51a in the flow waveform 51, for example as shown in FIG. 5a. The inspiratory phase occurs between the expiration to inspiration transition (see e.g. 51d) and the inspiration to expiration transition (see e.g. 51c). The method and/or apparatus of the present disclosure can provide improvements in the therapeutic application of medical treatments, but may also be used in instrumentation or diagnostic devices generally that monitor respiratory flow directly or indirectly. For example, in a Continuous Positive Airways Pressure (CPAP) device the air flow signal includes a leakage flow through a patient mask exhaust port. This leakage flow through the exhaust port offsets the respiratory flow signal away from the natural threshold that marks the transition between expiration and inspiration and vice versa.

A measured flow signal may also be distorted by other non-linear effects, for example, non-linear effects in the blower and inspiratory conduits, especially if the flow sensor (for example an ultrasound differential pressure sensor that measures flow, however, other appropriate sensors may be used, such as a sensor in the blower unit) is pressure differential based and placed some distance from the patient. The method of the present disclosure seeks to minimize these further effects in the determination of the respiratory phases.

Figure 4A:
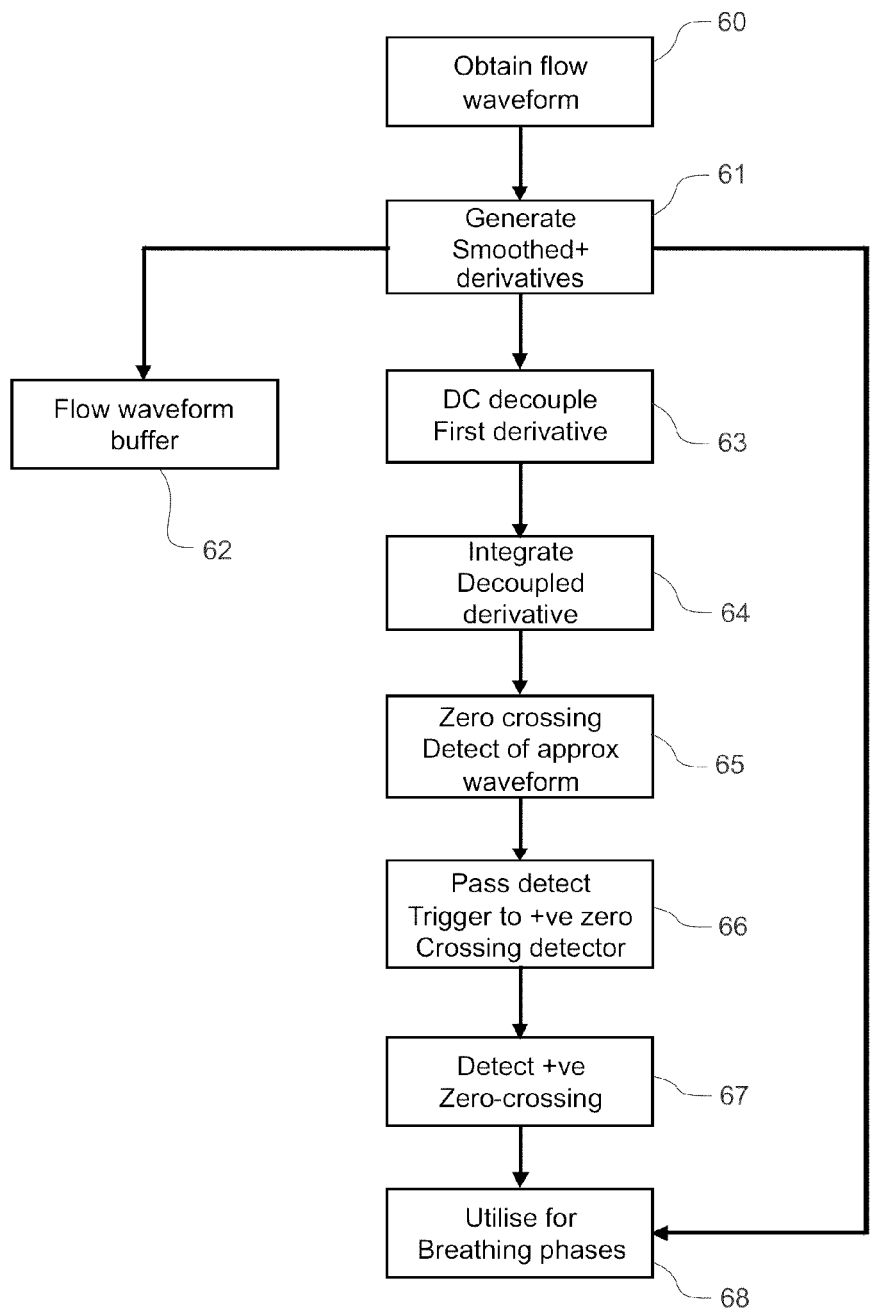
FIG. 4a illustrates a flow diagram of a method of an embodiment for determining breathing transitions.
Figure 4B:
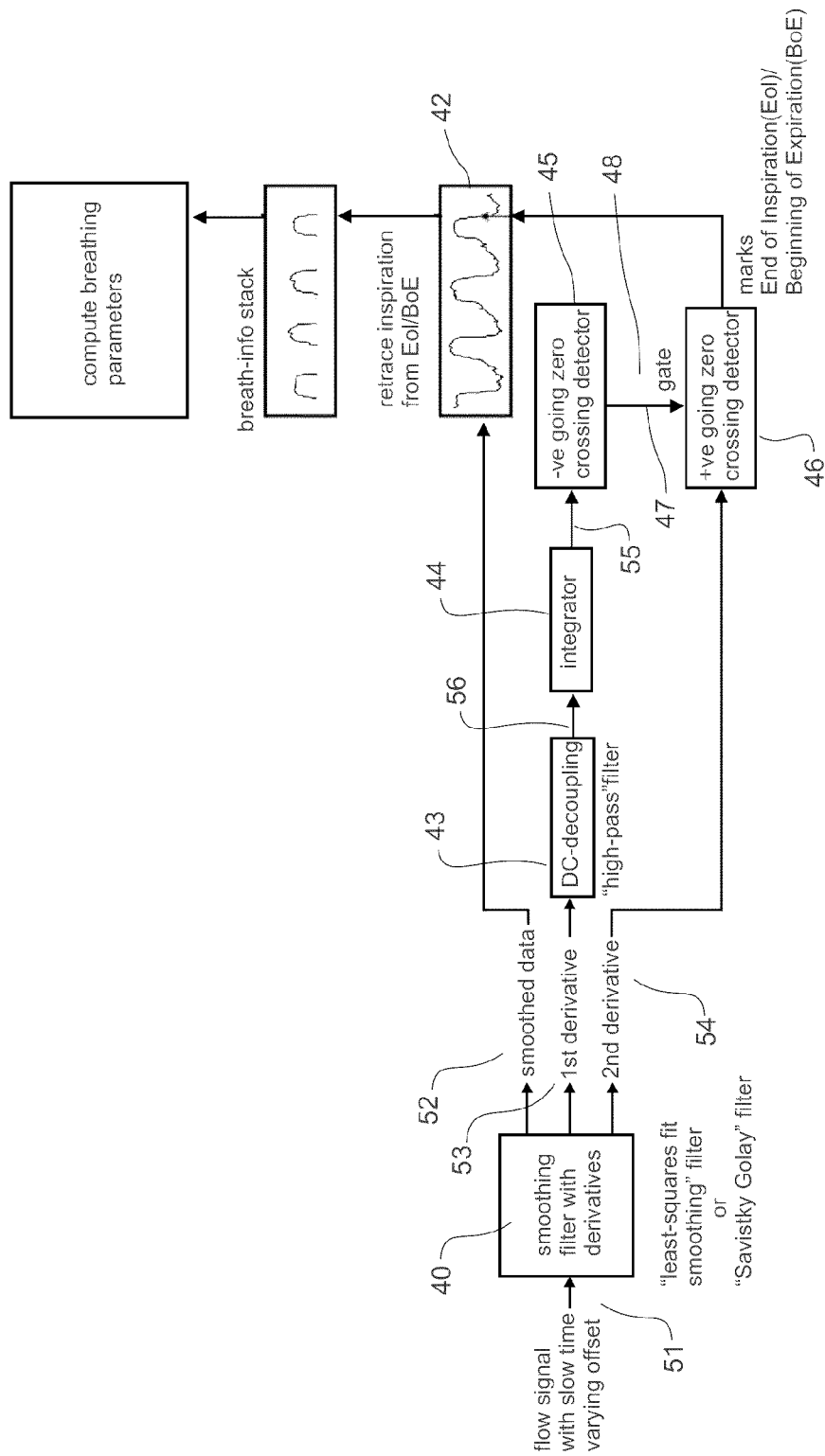

A method according to one embodiment will be described with reference to FIGS. 3 to 5g. FIG. 3 shows a humidified Positive Airway Pressure (PAP) system as described earlier. FIG. 4a shows a flow diagram of the algorithm that makes up this embodiment. FIG. 4b is a block diagram showing the functional blocks of hardware and/or software that implement this embodiment. The method can be implemented by a controller of the system in FIG. 3, such as the controller 9 or 18, or some other dedicated controller. The controller controls the system shown in FIG. 3 to carry out the various steps of the method, to be described below. The controller might execute software/firmware to implement the method, or it might be "hardwired" with the appropriate functionality shown in FIG. 4b. Those skilled in the art will appreciate that there are many alternatives for hardware and/or software design to implement the method described below. In an embodiment, the method is implemented in real-time or substantially real-time, such that as the patient breaths, their respiratory flow is monitored and transitions are detected as and when they occur. However, it is not essential that the method occurs in real-time.

FIGS. 5a to 5g show various waveforms that are generated in order to determine the inspiration to expiration transition (e.g. 51c) according this embodiment. It will be appreciated that not all these waveforms are essential in determining the transition. In alternative embodiments, only some of these waveforms might be generated and used.

Referring to FIGS. 5a to 5g, the following waveforms are shown, being waveforms representing or being derived from one or more electrical sensors measuring flow rate.
1. A flow waveform 51, which is the flow rate versus time of the patient's respiration (FIG. 5a). This shows expiration phases (e.g. 51b), inspiration phases (e.g. 51a), inspiration to expiration transitions (e.g. 51c) and expiration to inspiration transitions (e.g. 51d). The waveform includes a DC offset due to for example positive air pressure bias. The waveform also contains noise.
2. A smoothed flow waveform 52, which is a filtered version of the flow waveform 51 (FIG. 5b). Much of the noise has been removed.
3. A first derivative waveform 53 with respect to time of the smoothed flow waveform 52 (FIG. 5c).
4. A second derivative waveform 54 with respect to time of the smoothed flow waveform 52 (FIG. 5d).
5. An approximate flow waveform 55, which is an integration with respect to time of the first derivative waveform 53 (FIG. 5e). This has the DC offset removed.
6. A decoupled first derivative waveform 56 (FIG. 5f).
7. A third derivative waveform 57 with respect to time of the smoothed flow waveform 52 (FIG. 5g).

The waveforms are embodied in or specified by electrical signals received from the electrical sensors. Any reference in this specification to a waveform or processing thereof can equally apply to the underlying electrical signal or signals that define or embody the waveform, where appropriate. It will also be appreciated that the waveforms referred to might be embodied in data stored in or processed by computing equipment. Again, reference in this specification to waveforms might in practice relate to the underlying data embodying the waveforms. These representations of the waveform will be understood by a skilled person, and therefore referring to waveforms in a general manner is appropriate here.

It will be appreciated that the above waveforms show a small number of cycles in patient respiratory, being a typical representation. In the present disclosure, only a small portion of this waveform might be analyzed at any one time. This will occur as the waveform is received as input or generated.

Therefore, the waveforms shown in FIGS. 5a to 5g typically will not be processed in their entirety, but might be processed as received. However, the portions of the waveforms in FIGS. 5a to 5g are depicted to illustrate more fully the nature of the waveforms and the features that are analyzed. The waveforms have multiple peaks and/or zero-crossings that define transition points and/or breathing phases. The reference numerals will only refer to one such peak/zero-crossing of each waveform. It will be appreciated that other peaks/zero-crossings in a waveform will be apparent to the skilled person due to the cyclical nature of the waveforms.

The negative-going peak 53a in the first derivative 53 corresponds to the steepest descent (greatest negative-going slope) 51c in the flow waveform 51 for an inspiration/expiration transition 51c. The positive-going zero-crossing transition 54a for the second derivative 54 corresponds to a minima 53a of the first derivative and also corresponds to the steepest descent 51c in the flow waveform 51. Thus, the timing of the zero-crossing 54a in the second derivative 54 corresponds to the steepest descent 51c in the flow waveform 51.

From this, the Applicant has devised a method for determining the transition. In broad terms, the method uses the smoothed flow waveform 52 and the second derivative waveform 54 (or alternatively is based on the relationship between the second 54 and first 53 derivative waveforms. More particularly, the method includes using the approximate flow waveform 55 (or other variant of the flow waveform where the offset is removed) to determine the approximate point or region 55a where the flow waveform 55 crosses zero from positive to negative. This will approximately relate to the point of steepest descent 51c in the flow waveform 51. The method then includes looking at the second derivative waveform 54 to determine a negative to positive zero-crossing 54a, in the vicinity of the detected zero-crossing 55a of the approximate flow waveform 55. This will indicate occurrence in time of the inspiration to expiration transition 51c. Since the precise flow level at this point in time is especially susceptible to noise effects due to the steepness of the transition, the level of the offset may be estimated by aggregating the individual levels of consecutive points. Optionally, the third derivative waveform is also used to determine the transition, by assisting in isolating a negative to positive zero crossing that relates to a transition.

Referring to FIGS. 3 to 5g, a first embodiment of a method and apparatus for carrying out the disclosure will be described in detail. Using a system such as that shown in FIG. 3, a flow waveform 51 (or a signal representing a flow waveform) is obtained of the patient's respiratory breathing by measuring their breathing using a sensor 11, 12 or similar. FIG. 5a shows an example of a typical waveform 51 indicating the measured respiratory flow of a patient. The respiratory flow is the flow-rate of air into and out of the lungs of the patient versus time. A positive flow-rate indicates inspiration 51a, while and negative flow-rate indicates expiration 51b of air from the patient's lungs. The flow waveform 51 will have an offset 50 from zero, the offset reflecting the quiescent flow that results from the bias leakage at the mask 2. In the case where the blower 21 may be controlled over time according to some algorithm, the quiescent flow will be a gradually varying function of time. As will be appreciated by those skilled in the art, in practice, the flow waveform 51 depicts a sampled version of the respiratory breathing.

Referring to FIG. 4b, the flow waveform 51 (which comes from an electrical signal or similar and is converted to or otherwise represented in data form) is passed to a processing means, such as the controller 9 or 18, which is implemented in hardware, software and/or firmware. FIG. 4b shows in block diagram form the functionality of the controller. First the flow waveform is passed to a smoothing filter 40 with derivatives. A suitable smoothing filter can be a "least squares fit" smoothing filter such as the "Savitsky Golay" filter. A "Savitsky Golay" filter is a sliding window computation of a polynomial fit that outputs a zero phase shift smoothed signal together with smoothed derivatives. The order of the polynomial determines the number of time derivatives. A cubic polynomial for example gives a smoothed flow signal waveform, and the first three time derivatives. Therefore, the polynomial provides the smoothed flow waveform 52, first derivative 53 and second derivative 54 waveforms as an output from the filter 40. The first derivative 53 of the flow waveform 53 is, by virtue of differentiation, a signal devoid of the constant offset present in the smoothed flow waveform 52 due to quiescent flow.

The smoothed flow waveform 52 is output to a buffer 42 for retaining a time window of the smoothed flow waveform 52 samples for later processing. The first derivative waveform 53 is passed to a DC decoupler or high pass filter 43, and the decoupled output (being a decoupled first derivative 56) of this is passed to an integrator 44. The decoupled and integrated output, which is the approximate flow 55, is passed to a negative-going zero-crossing detector 45. The second derivative waveform 54 is fed into a positive-going zero-crossing detector 46. The negative-going zero-crossing detector 45 outputs a trigger signal 48 when a negative crossing is detected, and this passed to a gate 47 of the positive-going zero-crossing detector 46. This output signal 47 provides a trigger for the positive-going zero-crossing detector 46 to look for a zero-crossing on an input second derivative waveform 54 signal in the time vicinity of the negative-crossing 55a detected on the approximate waveform 55 by the negative zero-crossing detector 45.

Referring to FIG. 4a, the method implemented by the functional blocks shown in FIG. 4b will be described in detail. FIG. 4a shows in a conceptual sense what is occurring. A flow waveform 51 is obtained by the system shown in FIG. 3, step 60. A smoothed flow waveform 52 is then generated from the flow waveform 51 by the filter 40, step 61. The filter 40 also produces and outputs the first 53 and second 54 derivative waveforms, step 61.

The smoothed waveform 52 is passed to the buffer 42, step 62, which retains sufficient of the waveform to allow retracing of the inspiration waveform once the end-of-inspiration (i.e. inspiration to expiration) transition 51c has been identified. The first derivative waveform 53 is DC decoupled using a high pass filter 43, step 63. This removes or substantially removes any residual offset which may arise over time, from changes in flow offset. This produces the decoupled first derivative 56 shown in FIG. 5f. The decoupled derivative 56 is integrated in the integrator 44, step 64, to give the approximate flow waveform 55, as shown in FIG. 5e. The decoupling and integration, steps 63, 64, remove any DC or near DC offset arising in the smoothed flow waveform 52 due to bias leakage at the mask 2. This results in the approximate flow waveform 55.

The negative-going zero-crossing 55a of the approximate flow waveform 55 is then detected using the detector 45, step 65. The zero-crossing detection identifies the approximate timing of the steepest decent 55a of the falling edge in the approximate flow waveform 55, which corresponds approximately with the end of inspiration 51c. This then identifies the approximate position in time of the negative to positive going zero-crossing 54a in the second derivative waveform 54. The trigger point for the approximate flow waveform zero-crossing 55a is passed to the positive zero-crossing detector 46, step 66. The second derivative waveform 54 is then passed to the positive-going zero-crossing detector 46. The positive-going zero-crossing 54a of the second derivative 54 waveform is then detected, step 67.

The second derivative waveform 54 can have many negative to positive zero-crossings, not all of which correlate to an inspiration to expiration transition. Therefore, a negative to positive zero-crossing of the second derivative waveform 54 is detected in the time vicinity correlating to the detected negative-going zero-crossing 55a of the approximate waveform 55. This correlates to the inspiration to expiration transition 51c. A local search in time identifies the position and timing of the corresponding zero-crossing 54a in the second derivative. To do this, the second derivative waveform 54 can be buffered. In effect, the zero-crossing 55a of the approximate waveform 55 helps narrow down the search for the zero-crossing 54a in the second derivative waveform 54, that zero-crossing providing a more accurate indication of the occurrence of an inspiration to expiration transition 51c. The determined inspiration to expiration transition can be used to determine breathing phases, step 68, to be described below.

Figure 9:
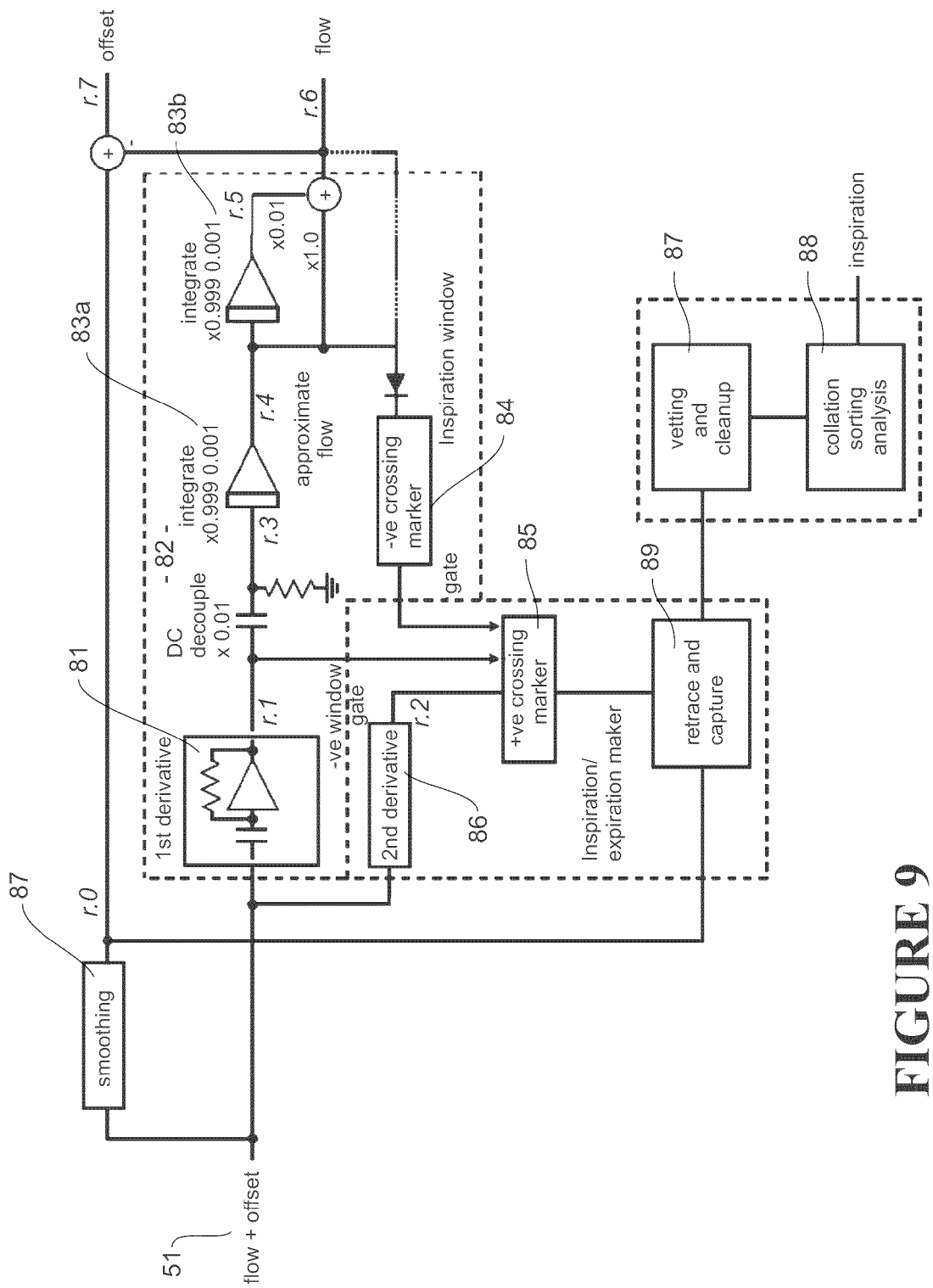
FIG. 9 is a more detailed block diagram showing an example implementation of the disclosure utilizing the detection of the steepest descent as a maker of the transition between the inspiration and expiration phase.

One implementation of this embodiment is shown in FIG. 9. The flow waveform 51 plus its inherent offset 50 is passed to a differentiator 81, the output being passed through a DC decoupler 82 and the output of that being passed to a first integrator 83a. The output of the first integrator 83a is the approximate waveform 55 and is passed to a zero-crossing detector 84, which outputs a trigger signal when a negative-going zero-crossing 55a is detected in the input waveform 55. This trigger is passed to a positive-going zero-crossing detector 85. The flow waveform 51 plus offset 50 is also passed to a second derivative differentiator 86 and the output 54 of this is also passed to the positive-going zero-crossing detector 85. The first derivative output 53 from the first differentiator 81 is also passed to the positive-going zero-crossing detector 85.

Based on triggers arriving from the negative-going zero-crossing detector 84, the positive-going zero-crossing detector 85 detects positive-going zero-crossings 54a in the input second derivative waveform 54. These relate to inspiration-to-expiration transitions 51c.

At this point, the transitions can then be utilized in any manner suitable for the particular application.

For example, it can be used to detect patient state. When a transition is detected in block 85, this information is fed to the retracing capture functionality 89. The resetting integrator of this block 89 computes the area (total displacement) under the inspiration, reset after each new breath. This provides a measure of the total inspiration as a function of the individual breaths. A centre of mass is computed for each inspiration phase and serves as a more robust means for assessing timing and the changes in inspiration (total volume as opposed to peak flow) from breath to breath. This provides a mechanism for reliably identifying hypopneas, and apneas.

The flow waveform 51 plus offset 50 is also passed through a smoothing block 87 the output of which is also passed to the retracing capture block 89. The output from block 89 is passed to a vetting and clean up block 87 and then on to a collation, sorting and analysis block 88 which outputs a signal indicating the inspiration phase. Blocks 87 and 88 represent signal processing (cleanup) steps that include determination of the awake/sleep state. This determination is based on the variance of the relative position of the "knee" being the level of the point corresponding to the change in slopes. These blocks can optionally also determine apneas, hypopneas, flow limitation, snoring events and the like.

A second integrator 83b can optionally be utilized, whereby the output of the first integrator is also provided to the input of the second integrator 83b. This provides a further correction. However, it has been found that the better solution is with the output of 83a since 83b is overly sensitive to fast changing flow offsets brought about by sudden changes to the blower speed control.

The core functionality of FIG. 9 including blocks 81, 82, 83a, and 84 obtains a negative going transition that closely identifies/estimates the period in time for the transition from inspiration to expiration. A more accurate result is then obtained by examining the second derivative positive going transition, as shown in FIG. 5d. The use of the zero crossing transitions in each of these steps affords a level of scale independence (to flow amplitude) and thus a robustness in the face of other influences and nonlinearities.

As mentioned above, once an inspiration to expiration transition 51c has been found, the present disclosure describes an embodiment of a method, software and/or apparatus for determining breathing phases of the patient. An inspiration breathing phase 51a of a patient occurs between an expiration to inspiration transition e.g. 51e and the next inspiration to expiration transition 51c. Similarly, the expiration breathing phase 51b of a patient occurs between an inspiration to expiration transition e.g. 51c and the next expiration to inspiration transition 51d. Once the inspiration to expiration transition 51c is found as described above, the next step in the method is to find the immediately previous or alternatively next expiration to inspiration transition 51e or 51d. This can be found by determining the flow-rate level at which inspiration to expiration 51c takes place and use this as a "virtual" zero level. The method then includes tracing backwards or forwards through the buffered flow waveform 51 at the same flow-rate level to determine where the waveform crosses the "virtual" zero level. At the immediate previous point in the flow waveform 51 where the waveform has a positive crossing through this virtual zero level indicates the immediate previous expiration to inspiration transition 51e. From this, it can be determined that an inspiration phase 51a has occurred between that expiration to inspiration transition 51e and a previously determined inspiration to expiration transition 51c. Similarly, the next expiration to inspiration transition 51d can be found by determining the next time at which the flow waveform 51 crosses the virtual zero level. The breathing phase 51b between the determined inspiration to expiration transition 51c and the determined next expiration to inspiration transition 51d defines an expiration phase 51b of the patient's breathing.

Therefore, the disclosure can optionally comprise determining the inspiration to expiration transition 51c, and from that inferring the expiration to inspiration transitions 51e, 51d occurring either side of the detected inspiration to expiration transition 51c. From this the inspiration 51a or expiration 51b breathing phases can be inferred. From this, the controller can operate the breathing apparatus in the desired manner to optimize operation for the various determined breathing phases to improve operation and improved comfort for the patient.

It will be appreciated that the above embodiment is one way of determining the inspiration to expiration transition. Alternatives are possible.

For example, the inspiration to expiration transition 51c can be simply found by looking directly at the second derivative waveform 54, without first finding the general region of the transition point 55a from the approximate waveform 55.

In another alternative, the inspiration to expiration 51c can be found from the negative peaks 53a in the first derivative waveform 53.

In another alternative, it would not be necessary to obtain the approximate waveform 55 to determine the approximate region 55a of the inspiration to expiration 51c. Rather a smoothed flow signal or other processed flow waveform can be used.

In another alternative, the first derivative negative peak 53a and the positive-going zero-crossing 54a of the second derivative waveform 54 can be used in combination to determine the inspiration to expiration 51c.

In another alternative, the inspiration to expiration transition 51c can be approximately obtained from the approximate waveform 55, without further referring to the first and/or second derivatives 53, 54.

In another alternative, the inspiration to expiration transition 51c can be approximately obtained from a DC decoupled flow waveform 55. However, DC decoupling the first derivative provides a better result.

In another alternative, it is possible to determine the expiration to inspiration transition 51c by a similar method, for example by looking at the positive to negative zero-crossing 54a of the second derivative, the negative peak 53a the first derivative and/or the steepest positive slope in the flow waveform 51c or wave form derived from it.

In another alternative, a third derivative 57 can be obtained and utilized, as shown in FIG. 6. This Figure depicts close up views of the approximate flow waveform 55 and the second and third derivatives 54, 50 in the region of the zero crossing/breathing transition. The third derivative 57 can be used, in conjunction with the zero crossing of the approximate waveform 55, to "isolate" the appropriate negative to positive zero crossing of the second derivative 54 that corresponds to the breathing transition. The third derivative will have a positive inverted peak 60, that crosses zero 61, 62 either side of the approximate flow waveform zero crossing. By "looking" in the region between the two zero crossings 61, 62 in the third derivative peak 60, the appropriate negative to positive zero crossing of the second derivative that corresponds to the breathing transition can be isolated from the other negative to positive zero crossings of the second derivative.

Figure 10:
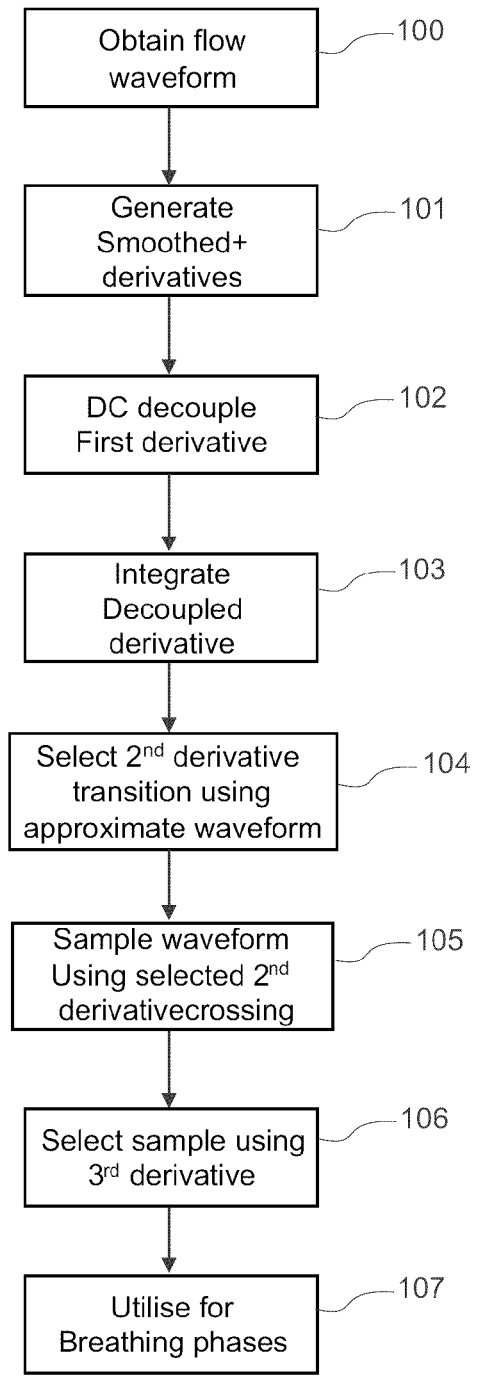
FIG. 10 illustrates a flow diagram of a method of a second embodiment for determining breathing transitions.
Figure 11:
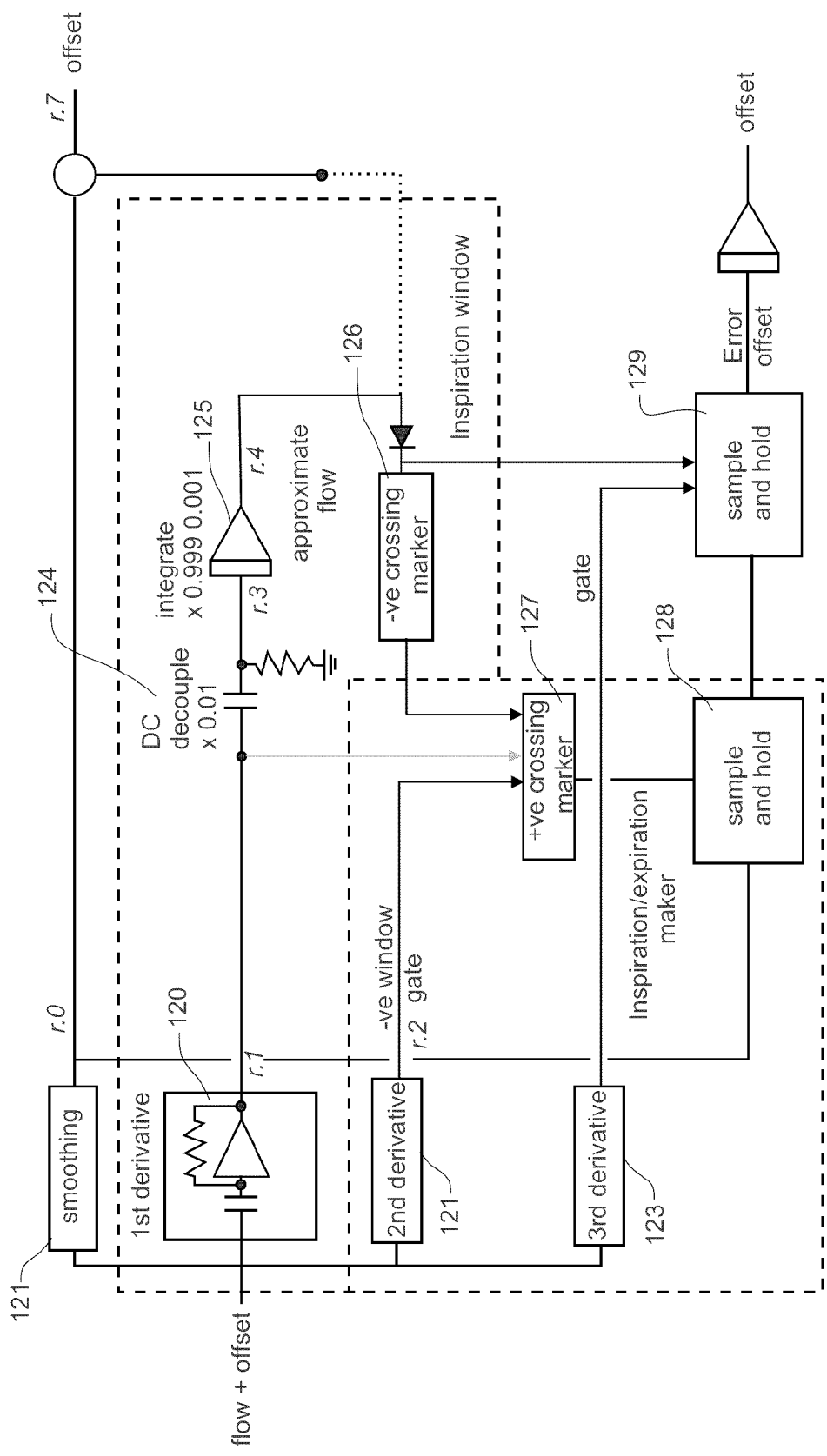
FIG. 11 illustrates a block diagram of a system for implementing the method of FIG. 10.
Figure 12:
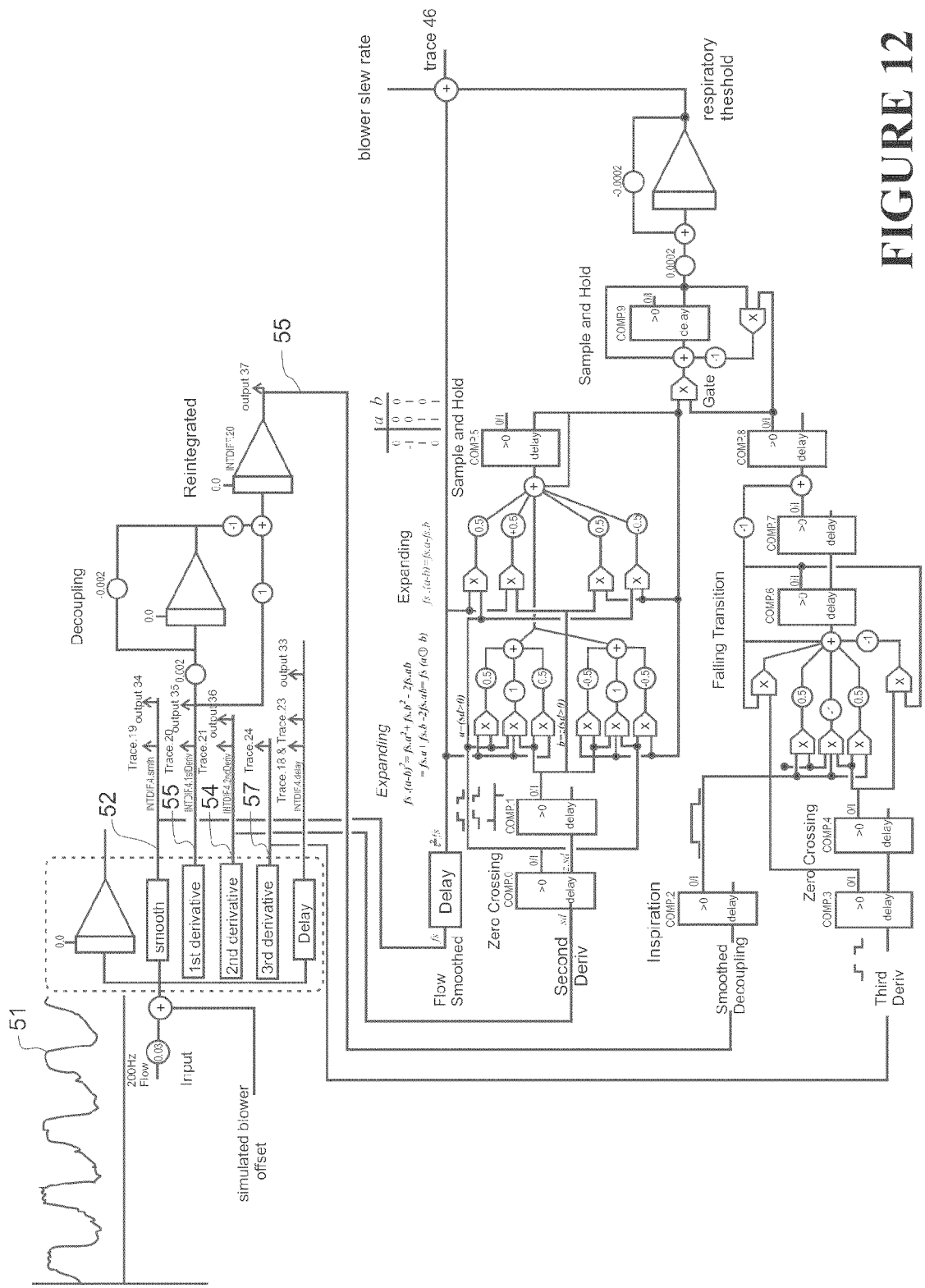
FIG. 12 illustrates one implementation of the second embodiment.

A second embodiment utilizing the third derivative is described in detail with respect to FIGS. 10 and 11. FIG. 10 shows a flow chart of a method carried out, while FIG. 11 shows in block diagram form the functionality of the controller 9 or 18 or similar for carrying out the method. One possible actual implementation is shown in FIG. 12.

Referring to FIGS. 10 and 11, a flow waveform (including offset) 51 is obtained, step 100, and then processed. The processing includes smoothing the flow waveform 51 to produce a smoothed waveform 52, and then generating first 53, second 54 and third 57 derivatives of the waveform, step 101. The flow waveform 51 is smoothed by filter 121, while the first, second and third derivatives are obtained from differentiators 120, 122, 123. The differentiators can be represented as shown in block 120, although this might not be their actual implementation. As noted in the previous embodiment, the derivatives can be obtained as a by-product of the filtering process. The first derivative is DC decoupled, step 102, using a high pass filter 124. The DC decoupled output is then re-integrated, step 103, in a first integrator 125 to produce the approximate flow waveform 55, which is smoothed and has the offset removed.

The approximate flow waveform 55 is used to select a positive going transition of the second derivative, step 104, which in turn is used to sample the smoothed flow waveform, step 105. Referring to FIG. 11, to do so, the output waveform 55 is passed to a negative going zero-crossing detector 126, which outputs a trigger signal when a negative-going zero-crossing 55a is detected in the input waveform 55. This trigger is passed to a positive-going zero-crossing detector 127. The second derivative output 54 of the second differentiator 121 is also passed to the positive-going zero-crossing detector 127. Based on triggers arriving from the negative-going zero-crossing detector 126, the positive-going zero-crossing detector 127 detects positive-going zero-crossings 54a in the input second derivative waveform 54 that occurs around breathing transition in the smoothed flow waveform 51 which also provides an estimate of the breathing transition in the flow waveform 51. These detections might relate to inspiration-to-expiration transitions 51c. Upon detection, a trigger signal is output. The trigger outputs from the positive going zero crossing detector 127 are used as input triggers to a first sample and hold block 128. This block also receives, as input, the smoothed flow waveform 52. Each detected positive zero crossing in the second derivative triggers a sample of the smooth flow waveform 52. This sample may or may not relate to a breathing transition in the flow waveform 52. As mentioned previously not all positive going zero crossings of the second derivative relate to breathing transitions.

Next, the third derivative 57 together with the negative going zero crossing of the approximate flow waveform 55 is used to determine which sample should be used from block 128, step 106. The third derivative output 57 from the third differentiator 123 is passed to a second sample and hold block 129. In addition, this block 129 receives as input the approximate flow waveform 55, and the sample and hold output from the first sample and hold block 128. The third derivative will have a positive peak and zero crossings that straddle the zero crossing in the approximate waveform 55. The negative going zero crossing of the third derivative 57 triggers the second sample and hold block 129 to capture the output from the first sample and hold block 128, being the previously sampled portion of the smoothed waveform sampled by the previous positive going second derivative zero crossing. (For this purpose, it is the negative going zero crossing of the third derivative that occurs after the zero crossing of the approximate flow waveform that is used.) There is only one positive zero crossing of the second derivative that falls within the positive region of the third derivative straddling the zero crossing of the approximate flow waveform 55, and this will be the zero crossing relating to breathing transition. Therefore, the positive going second derivative zero crossing immediately prior to the negative going zero crossing of the third derivative will correspond to the breathing transition, and as such the portion of the smoothed waveform it sampled will correspond to the breathing transition. In effect, the third derivative "gates" the second derivative positive going crossings to leave the crossing corresponding to a breathing transition. The value of the smoothed flow waveform that is sampled at that point is deemed to be the best estimate of the offset at the transition from inspiration to expiration. This value can be used to determine the timing of subsequent inspiration to expiration transitions. The identified transitions can be used to determine breathing phases and/or device control as described with respect to the first embodiment, step 107

FIG. 12 shows an actual implementation of the functionality shown in FIG. 11, which carries out the method of FIG. 10. This shows the logical implementation that can implemented using an analog computing package or similar.

In the specification, where the inspiration to expiration or expiration to inspiration transition is mentioned, it will be understood by those skilled in the art that this might not technically relate to a single point. The tolerances in the system determining this point might be such that an inspiration to expiration or expiration to inspiration region is determined. While this may not be as accurate, this may still provide sufficient accuracy of the inspiration to expiration transition to provide a useful system.

Some of the embodiments of the present disclosure use techniques to eliminate or minimize dependencies of scale in respect of the signal dynamics of a respiratory flow signal. In this respect the use of arbitrary reference levels or thresholds are avoided. Thus, in an embodiment of this disclosure the reference threshold of choice is zero, and the steps of determining the transitions between the respiratory phases thus reduces to identifying appropriate points in time when either negative- or positive-going zero-crossings occur.

The method of the present disclosure provides more accurate indications of zero crossings, reducing sensitivity to time related transients and time scale effects through the use of least squares fit smoothing filters that also provide smoothed derivatives of the flow signal.

The Applicant has found the algorithm of the present disclosure operates robustly across a range of sampling rates, by suitably optimizing time scale dependencies arising by way of the filtering functions. In the one embodiment the algorithm is targeted to known sampling rates in the range of 50 to 500 Hz.

Determining the breath transition has many useful applications in the area of PAP apparatus. The breathing state of a person may be monitored for a variety of reasons, for example to check if she/he is awake or asleep, if she/he is snoring or if she/he is suffering from apnea, or hypopnea. If the person is snoring or suffering from apnea and/or hypopnea then measures may or even must be taken. The pressure of the supplied air can be changed for example, and if this does not lead to a desired result, then a wake-up signal can be generated.

Airflow will have a strong amplitude modulation when a person is snoring. Therefore, according to a further aspect of the disclosure, the first derivative of the electrical signal is rectified during the inspiration phase and subsequently compared with a third threshold, for determining a snoring situation.

It has been noticed that for a sleeping person the flow of air during the expiration phase consists of two sub phases having different slopes. Preferably the smoothed second derivative of the electrical signal is used to locate the point in time when the slope changes, and the degree of fluctuation, or conversely the stability from breath to breath in the flow level at the point in time where the change in slope occurs is used for determining if a person is awake or asleep.

What is claimed is:

1. A system for determining the transition between inspiration and expiration of a patient's respiratory cycle comprising:
    a flow sensor for measuring a patient's respiratory flow to obtain a flow waveform indicative of the respiratory flow; and
    an electronic device to determine a second derivative of the flow waveform or part thereof, and determine an inspiration/expiration transition of the patient's respiratory flow by identifying the steepest descent in the flow waveform using the second derivative of the flow waveform;
    wherein to determine an inspiration/expiration transition of the patient's respiratory flow using the second derivative the electronic device uses a negative to positive zero crossing in the second derivative; and
    wherein the flow waveform has an offset and the electronic device is adapted to
        detect a zero crossing of the flow waveform without an offset,
        wherein to use a negative to positive zero crossing in the second derivative the electronic device uses a negative to positive zero crossing in the second derivative that corresponds to the zero crossing in the flow waveform.

2. A system according to claim 1 wherein the electronic device obtains a third derivative of the flow waveform or part thereof, wherein to use a negative to positive zero crossing in the second derivative the electronic device uses a negative to positive zero crossing in the second derivative that corresponds to the zero crossing in the flow waveform and a positive portion of the third derivative that coincides with the flow waveform and second derivative zero crossings.

3. A method of determining the transition between inspiration and expiration of a patient's respiratory cycle comprising:
    measuring a patient's respiratory flow using a flow sensor to obtain a flow waveform indicative of the respiratory flow;
    sampling, using an electronic controller, at least a portion of the flow waveform using negative to positive zero crossings of a second derivative of the flow waveform; and
    selecting, using the electronic controller, one of the samples using a third derivative of the flow waveform as a trigger, the selected sample identifying a breathing transition.

4. A method according to claim 3 wherein a positive to negative zero crossing of the third derivative is used as the trigger.

5. A system for determining the transition between inspiration and expiration of a patient's respiratory cycle comprising:
    a flow sensor for measuring a patient's respiratory flow to obtain a flow waveform indicative of the respiratory flow; and
    an electronic device to sample at least a portion of the flow waveform using negative to positive zero crossings of a second derivative of the flow waveform, and to select one of the samples using a third derivative of the flow waveform as a trigger, the selected sample identifying a breathing transition.

6. A system according to claim 5 wherein a positive to negative zero crossing of the third derivative is used as the trigger.

* * * * *